US006995240B1

(12) United States Patent
Panayi et al.

(10) Patent No.: US 6,995,240 B1
(45) Date of Patent: Feb. 7, 2006

(54) TREATMENT OF INFLAMMATORY DISEASE

(75) Inventors: Gabriel Stavros Panayi, London (GB); Valerie Mary Corrigall, Tadworth (GB); Mark Duncan Bodman-Smith, London (GB); Mark Stewart Fife, London (GB); Jeremy Shaun Lanchbury, Tunbridge Wells (GB)

(73) Assignee: King's College London, (GB)

( * ) Notice: Subject to any disclaimer, the term of this patent is extended or adjusted under 35 U.S.C. 154(b) by 0 days.

(21) Appl. No.: 09/806,955

(22) PCT Filed: Oct. 8, 1999

(86) PCT No.: PCT/GB99/03316

§ 371 (c)(1),
(2), (4) Date: Jul. 11, 2001

(87) PCT Pub. No.: WO00/21995

PCT Pub. Date: Apr. 20, 2000

(30) Foreign Application Priority Data

Oct. 9, 1998  (GB) .................................. 9822115

(51) Int. Cl.
*C07K 14/47* (2006.01)
*A61K 39/00* (2006.01)
*G01N 33/53* (2006.01)

(52) U.S. Cl. ................ 530/350; 424/184.1; 424/185.1; 435/7.1; 435/810

(58) Field of Classification Search ................ 530/350; 424/185.1, 184.1; 435/810, 7.1
See application file for complete search history.

(56) References Cited

U.S. PATENT DOCUMENTS 5,188,964 A * 2/1993 McGuire et al.
5,348,945 A * 9/1994 Berberian et al.

FOREIGN PATENT DOCUMENTS

WO   WO 94 08012 A   4/1994
WO   WO 99 18131 A   4/1999
WO   WO 99 53040 A   10/1999

OTHER PUBLICATIONS

NCBI Protein Accession No. p11021. 78 KDA Glucose-Regulated Protein Precursor (GRP 78) (Immunoglobulin Heavy Chain Binding Protein GRP78).*
Hsu et al. Protein Expression and Purification, (1994) vol. 5, No. 6, pp. 595-603.*
Witzmann et al. Fundamental and Applied Toxicology, (1994) vol. 23, No. 1, pp. 1-8.*
Haas et al. Proc Natl Acad Sci U S A, (1988) 85 (7), 2250-2254.*

Kozutsumi et al. Journal of Cell Science. Supplement, (1989) 11 115-37.*
Geiger et al. (Journal of Rheumatology Nov. 1994; 21(11): 1992-1997).*
Malfait et al. (Journal of Immunology May 1999; 162(10: 6278-6283).*
Mikayama et al. (PNAS, 1993. 90: 10056-10060).*
Ngo et al, in The Protein Folding Problem and Tertiary Structure Prediction, 1994. (ed.), Birkhauser, Boston, MA, pp. 433 and 492-4.*
Sambrook et al. (Molecular Cloning: A Laboratory Manual (1989) Cold Spring Harbor Laboratory Press, New York; p. 17.2).*
Hass, I.G., Experientia 1994; 50(11-12):1012-1020.*
Munro and Pelham Cell 1986; 46:291-300.*
Leborgne-Castel, N. et al., "Overexpression of BiP in tobacco alleviates endoplasmic reticulum stress." *The Plant Cell*, vol. 11, No. 3, Mar. 1999, pp. 459-470, XP002131460.
St. Blass, et al., "The rheumatoid arthritis-associated autoantigen p68 identified as heavy chain binding protein (BIP." *Arthritis & Rheumatism*, vol. 42, No. 9, Sep. 1999, Suppl., p. S244, Meeting Info: 63$^{rd}$ Annual Scientific Meeting of the American College of Rheumatology and the 34$^{th}$ Annual Scientific Meeting of the Association of Rheumatology Health Professionals, XP002131445, abstract.
Ting, J., et al., "Human gene encoding the 78,000-dalton glucose regulated protein and its pseudogene: structure conservation and regulation." *DNA*, vol. 7, No. 4, pp. 275-286, XP000877141.
Macario, A., "Heat-shock proteins and molecular chaperones: implications for pathogenesis, diagnostics, and therapeutics." *Int.J. Clin. Lab Res.*, vol. 25, pp. 59-70, 1995.
Bläβ, S., et al. "Novel 68 kDa autoantigen detected by rheumatoid arthritis specific antibodies." *Ann. Rheum. Dis.*, vol. 54, pp. 355-360, 1995.
Bläβ, S., et al. "Rheumatoid arthritis: autoreactive T cells recognising a novel 68k autoantigen." *Ann. Rheum. Dis.*, vol. 56, pp. 317-322, 1997.
Bläβ, S., et al. "The p68 autoantigen characteristic of rheumatoid arthritis is reactive with carbohydrate epitope specific autoantibodies." *Ann. Rheum. Dis.*, vol. 57, pp. 220-225, 1998.

* cited by examiner

*Primary Examiner*—Phillip Gambel
*Assistant Examiner*—Ilia Ouspenski
(74) *Attorney, Agent, or Firm*—Joseph T. Leone, Esq.; DeWitt Ross & Stevens S.C.

(57) ABSTRACT

The immunoglobulin heavy chain binding protein BiP (GRP78), or a fragment thereof, provides a reagent for indicating the presence of rheumatoid arthritis (RA). The protein used is a recombinant BiP(GRP78) having a defined sequence. A prognostic and/or diagnostic test for RA may be an ELISA or a Western Blot that utilizes the BiP(GRP78) protein or a fragment thereof. Also disclosed are a method of testing for RA using BiP(GRP78) or a cDNA sequence coding therefor. Further disclosed is a method of treating RA by the BiP(GRP78) protein or corresponding cDNA.

15 Claims, 3 Drawing Sheets

FIG. 1

TREATMENT OF INFLAMMATORY DISEASE

Priorty is hereby claimed to PCT application Ser. No. PCT/GB99/03316, filed Oct. 8, 1999.

FIELD OF THE INVENTION

This invention relates to inflammatory disease and more particularly to rheumatoid arthritis.

BACKGROUND

Rheumatoid arthritis (RA) is a chronic inflammatory disease of the synovial joints which leads to joint destruction, disability and early death. Although the cause of RA is presently unknown, it has been suggested that type II collagen, uniquely found in the articular cartilage, is a possible autoantigen for RA. It has recently been proposed that gp39, a 39 KD glycoprotein, and peptides derived from it, are such autoantigens. However, the data supporting this hypothesis are limited and the role of gp39 therefore remains uncertain.

The present invention stems from a different approach based on a study of chondrocytes, the specialised cells of articular cartilage. We have isolated a protein from human chondrocytes and human chondrosarcoma cell lines which reacts with antibodies present in RA patients' sera and meets the accepted criteria for a putative autoantigen. This purified protein has been tested for proliferation of T cells and has been shown to selectively proliferate synovial T cells from patients with RA. This protein is the immunoglobulin heavy chain binding protein BiP(78 KD).

International patent application WO 99/18131 proposes the detection of antibodies to a BiP deriving from Hela cells as a diagnostic indication of RA. However, this prior disclosure does not describe the extraction of BiP from the Hela cells in a reproducible manner and is therefore insufficient for practical application.

SUMMARY OF THE INVENTION

The first part of the following description concerns the characterisation of such an autoantigen; the second the cloning sequencing and expression of the protein; and the third part the demonstration of disease (rheumatoid arthritis) and tissue (synovial compartment) T cell specificity to the autoantigen.

DETAILED DESCRIPTION OF THE INVENTION

Part 1: Characterisation of Autoantigen

Chondrocytes/Chondrosarcoma Cells

Chondrocytes were isolated from cartilage obtained during joint replacement. The cartilage was minced finely and digested with 1 mg/ml collagenase (Worthington). Following digestion the cells were centrifuged at 300 g and resuspended in Dulbeccos minimal essential medium (DMEM)(Life Technologies, Paisley, UK) enriched with 10% foetal calf serum (FCS)(Harlan Sera-Lab, Loughborough, UK). Cell debris was washed off the adherent cells after 24 hours and the cells allowed to expand until confluent. Cells were passaged using trypsin (0.25%) and split 1:3.

Chondrosarcoma cells (HTB94) (SW1353) were supplied by the American Type Culture Collection ATCC (Rockville, Md., USA) and by Dr J Block, Rush University, Chicago, USA (personal gift). These cells were cultured in DMEM with 10% FCS and split 1:3 after gentle trypsinisation (0.25% trypsin Life Technologies, Paislev, UK) when confluent.

Preparation of Cell Lysates

Cells were scraped from the flask surface, homogenised and sonicated in the presence of proteinase inhibitors PMSF (2 mM), leupeptin (200 $\mu$g/ml) and aprotinin (50 $\mu$g/ml) (Sigma, Poole, UK).

Sodium dodecyl sulphate (SDS) (Sigma, Poole, UK) was added to a final concentration of 1% and the proteins solubilised at room temperature for 1 hour. Protein concentration was estimated by bicinchonimic acid assay using bovine serum albumin (BSA) as a standard protein (Sigma) and the cell lysate was used at 10 $\mu$g/well equivalent.

Polyacrylamide Gel Electrophoresis (PAGE) and Western Blot

The Mini Protean system (BioRad Laboratories. Hemel Hempstead, UK) was used to run the gels. 5. 7.5 or 10% SDS polyacrylamide denaturing gels 1.5 mm thick were prepared (See Appendix 1). Gels were loaded with 10 $\mu$g protein/well or the equivalent was loaded on preparative gels. Electrophoresis was carried out at a constant 100V and broad range kaleidoscope markers (BioRad) were run in parallel with the cell lysates.

Following electrophoresis the proteins were blotted onto nitrocellulose at a constant 100V for 1 hour (See Appendix 1). Nitrocellulose was then blocked with 3% BSA (Sigma, Poole,UK) and left at 4° C. overnight. Preparative gel membranes were cut into 16 thin strips when necessary, each having an identical protein profile. The membranes were probed with patients sera (1/100 dilution) or specific monoclonal antibodies (at required concentrations) for 1 hour at room temperature and then washed ×3 over 1 hour in TTBS (See Appendix 1). The secondary antibody, goat anti-human IgG (Fab$^2$) horse radish peroxidase(HRP) conjugate (Sigma) was added at 1/1000 dilution and incubated for 1 hour at room temperature. The membranes were then washed ×3 over 1 hour in TTBS. Enhanced chemiluminescence (Amersham)

was used to develop the system and antigen-antibody HRP complexes appeared as discrete bands on photographic film when developed.

Isolation of the Putative Autoantigen p78

The band of interest was seen in approximately 30% of the rheumatoid arthritis sera used to screen the cell lysates as previously described.

To isolate the protein the cell lysate was concentrated ×23, using a 30.000 MW cut-off filter(Vivascience). This protein was then loaded on 5% and 7.5% gels in parallel. One lane on each was loaded at normal concentration while the two other lanes were overloaded with the protein. Kaleidoscope markers were loaded on either side of the test lanes. The gels were then run as previously described until the kaleidoscope markers showed that the 70,000 MW protein would be in the bottom third of the gel as close as possible to the run-off point. The gels were then blotted onto PVDF membrane (Immobilon P. Millipore) which was immediately placed in distilled water after transfer of the proteins was complete. The strip with normal loading was used for immunodetection of the protein band. The developed film of this immunodetection and Ponceau red staining of the overloaded strips was used to identify the band on the membrane which was then air-dried.

These strips were then taken to isolate and sequence the protein using matrix assisted laser desorption ionisation (MALDI) spectroscopy.

The electroblotted proteins were stained with Ponceau S (0.05% w/v aqueous methanol/0.1% acetic acid) using a rapid-staining protocol (1). The dried, stained proteins were then digested in situ with trypsin (Boehringer, modified) and the peptides extracted with 1:1 v/v formic acid:ethanol (2). One 0.2 µl aliquot (approximately 5% of the total digest) was sampled and directly analysed by matrix-assisted laser desorption ionisation (MALDI) time-of-flight mass spectrometry using a LaserMat 2000 mass spectrometer (Thermo Bioanalysis,UK) (3). A second 0.2 µl aliquot was quantitatively esterified using 1% v/v thionyl chloride in methanol and also analysed by MALDI to provide acidic residue composition (4). Native and esterified peptide masses were then screened against the MOWSE peptide mass fingerprint database (5). The remaining digested peptides (90% of total digest) were then reacted with N-succinimidyl-2 (3-pyridyl) acetate (SPA) in order to enhance b-ion abundance and facilitate sequence analysis by tandem mass spectrometry (6). Dried peptide fractions were treated with 7 µl 1% w/v N-succinimidyl-2(3-pyridyl) acetate in 0.5M HEPES (pH 7.8 with NaOH) containing 15% v/v acetonitrile for 20 min on ice. The reaction was terminated by 1 µl heptafluorobutyric acid (HFBA) and the solution immediately injected onto a capillary reverse-phase column (300 µm×15 cm) packed with POROS R2/H material (Perseptive Biosystems, MA) equilibrated with 2% v/v acetonitrile/0.05% v/v TFA running at 3 µl/min. The absorbed peptides were washed isocratically with 10% v/v acetonitrile/0.05% v/v TFA for 30 minutes at 3 µl/min to elute the excess reagent and HEPES buffer. The derivatised peptides were then eluted with a single step gradient to 75% v/v acetonitrile/0.1% v/v formic acid and collected in a single 4 µl fraction. The derivatised peptides were then sequenced by low-energy collison-activated dissociation (CAD) using a Finnigan MAT TSQ7000 fitted with a nanoelectrospray source (7,8). CAD was performed using 2.5 mTorr argon with collisonal offset voltages between −18V and −28V. The product-ion spectra were collected with Q3 scanned at 500 amu/sec.

RESULTS

Sequence data obtained from 7.5% gel (single band) from GR78_human Specific identifying peptides:

Part 2: Cloning, Sequencing and Expression of p78

1) mRNA Isolation and PCR Amplification of Identified Genes.

Human chondrocytes were isolated and cultured for three weeks as described. Poly(A) mRNA (1-2 µg) was extracted with a Micro-Fastrack kit (Invitrogen) from a total of 1–2×10$^6$ cells. One microgram of the resulting mRNA was reverse transcribed into cDNA in a 20 µl volume at 45° C. for 1 hour using 1 µl of Moloney murine leukemia virus reverse transcriptase (200 u/µl ); 5×first strand buffer (Tris-HCl pH 8.3, 250 mM; KCl 375 mM; MgCl 15 mM); 0.1M DTT; oligo dT(12–18) 20 ng/µl (Life Technologies); and dNTP mix 100 mM (Amersham Pharmacia Biotec, Uppsala Sweden).

PCR was performed in a 50 µl reaction volume under standard conditions (see below) using a Perkin Elmer Applied Biosystems thermal cycler PE2400. Primer sequences were derived from the GenBank database sequence corresponding to the Human gene for the immunoglobulin heavy chain binding protein, Bip (grp78), accession number X87949. Specific primers were synthesized to amplify the putative autoantigen gene from the chondrocyte cDNA. The resulting PCR product consisted of most of the grp78 coding region, bar the untranslated regions, signal sequences and the stop codon (nucleotide positions 279–2169 of the grp78 database sequence).

Primer sets for PCR were designed with integrated restriction sites to allow rapid subcloning of cDNA into the bacterial expression vector. The Forward primers encoded an NdeI site and the Reverse primers contained an XhoI restriction site: The Sequence Listing for the forward primer is given hereafter as SE4 and that for the reverse primer is given as SE5.

Bip Forward Primer:
5'-TATACATATGGAGGACAAGAAGGGAGGACG-3'
(SEQ ID NO: 4)

Bip Reverse Primer
5'-CCACCTCGAGTTCTCGTGTATCCTCTTCACCA-3'
(SEQ ID NO: 5)

After initial denaturation at 96° C. for 2 min the, PCR was performed for 28 cycles using a cycling profile of 94° C. for 30s, 60° C. for 30s and 72° C. for 2 min, with a final extension at 72° C. for 7 min. The PCR reaction generated a single specific Bip fragment of 1890 bp.

2) Cloning of PCR Generated Fragments.

The restriction sites engineered into the forward and reverse primers used for the PCR reactions required flanking DNA for them to be recognised by their specific endonucleases (NdeI and XhoI). To provide this flanking DNA, the PCR generated fragment was cloned into a PCR cloning vector pCR2.1-TOPO (Invitrogen). The ligated plasmids were transformed into competent E. coli XLI-Blue (Stratagene) and plasmid DNA extracted using miniprep purification columns (Qiagen). The purified plasmid DNA for the clone was designated Bip-Topo. These DNA samples were stored at −20° C. The purified plasmid DNA for Bip-Topo was digested with NdeI and XhoI. The restricted fragments were separated by agarose gel electrophoresis and purified using the Qiagen DNA gel extraction kit.

3) Subcloning of Restricted Gene Fragments into Bacterial Expression Vector.

The purified fragment for the clone was ligated into the NdeI/XhoI pre-digested bacterial expression vector pET30a (Novagen). Ligation was performed at 12° C. overnight in the presence of T4 ligase (20 units) and ⅒ vol of 10× ligase buffer (provided with the T4 ligase enzyme from Promega). The ligated plasmids were transformed into competent *E. coli* XL1-Blue (Stratagene) and screened by colony-PCR using Bip specific primers. Positive transformants carrying the required recombinant plasmids were purified and transformed into competent *E. coli* expression strain BL21-(DE3) (Invitrogen).

It will of course be understood that cloning may be carried out in prokaryotic or eukaryotic hosts including bacteria, insect cells, and mammalian cells. Preferred hosts are those which ensure glycosylation of the expressed product.

4) Sequencing of the 1890 bp pET30::Bip Subclone.

Sequencing of the 5' and 3' terminal ends of the pET30a::Bip clone confirmed that the recombinant DNA molecule was in-frame with the ATG start codon on the pET30 vector and that readthrough from this site continued through the Bip gene and ended with the 6×His residues and the stop codon located on the 3' arm of the expression vector.

Extensive DNA sequencing was performed using synthetic oligonucleotide primers spanning the entire length of the Bip subclone. Sequence analysis of the newly subcloned Bip gene fragment was performed by comparative alignment against the existing grp78 sequence from the database (accession number X87949). A number of differences between the two sequences were detected, both at the DNA and protein level (see Appendix 2). These areas of disagreement may either be a result of errors in the original DNA sequencing (of grp78) or they may indicate the presence of an additional related, but slightly different Bip gene in the genome.

All DNA sequencing was performed on an Applied Biosystems ABI 377 automated DNA sequencer using the dRhodamine dye terminator kit (Perkin Elmer-Applied Biosystems).

Expression of Bacterial and Purification Recombinant Proteins.

*E. coli* expression strain BL21-(DE3) containing the recombinant pET30a-Bip plasmid was grown at 37° C. in LB medium containing kanamycin (50 g/ml). When the cells had reached an $OD_{600}$ of 0.6 units, isopropyl β-D-thiogalactopyranoside (IPTG) (1 mM) was added to the medium to induce expression of the recombinant protein, driven by the IPTG-inducible promoter of the expression vector. To allow for maximal expression of the recombinant protein the culture was incubated for a further 4 hours at 37° C. The cells were pelleted by centrifugation and stored at −70° C.

For purification of the recombinant bacterial proteins the bacterial pellets were lysed in binding buffer (20 mM $NaPO_4$, 500 mM NaCl. 5 mM Imidazole, 1 mM PMSF, 1 mg/ml Lysozyme, 5 units/ml DNAse, 0.1% Triton X-100, pH7.4). The lysate was cleared by centrifugation to remove insoluble matter and cell debris. The cleared lysate was passed over a binding buffer-equilibrated chelating Hi-trap affinity column, with a bed volume of 5 ml (Pharmacia). The non-specifically bound protein was washed from the column under stringent conditions using a series of three wash buffers. The primary wash was performed using 100 ml of Binding buffer. This was followed by a high stringency low pH wash (20 mM $NaPO_4$, 500 mM NaCl, 0.1% Triton X-100, pH5.5) and an additional high stringency wash using 100 ml of 20 mM $NaPO_4$, 500 mM NaCl, 0.1% Triton X-100, 50 mM Imidazole, pH7.4.

The histidine-tagged recombinant proteins were eluted from the column by stripping with 50 mM EDTA. Eluted proteins were dialysed overnight against 1×PBS to remove EDTA and Ni contaminants. The purified protein was concentrated and washed in sterile PBS using a 50000 Mw cutoff concentrator column (Millipore). The total amount of protein was determined by spectrophotometry using BSA as a standard with the bicinchonimic acid assay.

Immunological Studies in Experimental Arthritis

Antibody response to p78 in experimental arthritis Collagen arthritis (CIA) and pristane arthritis (PLA) were induced in DBA/1 mice according to our previously described protocol. Mice were bled before induction of arthritis (15 animals), at the onset of CIA (16 anials) and the onset of PIA (14 animals). The antibody in mouse sera against p78 was determined using an enzyme-linked immunosorbent assay (ELISA) with recombinant p78. Nunc 96-well ELISA plates (Fisher Biotech, Orangeburg, N.Y.) were coated overnight at 4° C. with p78 at 500 ng (in 100 ml of 5% non-fat milk/PBS) per well. After washing 3 times with phosphate buffered saline (PBS) containing 0.05%, Tween-20, the plate was blocked with 5% non-fat milk/PBS overnight at 4° C. The mouse sera were added into the wells at 1:200 dilution in milk/PBS and incubated overnight at 4° C. The plate was washed, 100 ml goat anti-mouse Ig conjugated with alkaline phosphatase (anti-Ig-AK: 1:500 dilution in milk/PBS/Tween-20, Fisher Biotec) was added for 60 mins at 37° C. After three washes with PBS/Tween-20, 100 ml paranitrophenyl phospphate solution (PNPP tablets; Sigma Chemicals; St Louis, Mo.) in diathylanolamine buffer was added to each well. The reaction was allowed to proceed for 30 mins in the dark and the plate read at 405 nm in aspectrophotometer (Molecular Devices, Menlo Park, Calif.). The data were analyzed using the SOFTmax analytical software package. The specific binding were the OD readings from p78-coated wells subtractinf the OD from non-coated as well as non-sera blanks. The antibody levels were expressed as $OD_{405}$ units.

RESULTS

Identification of Autoantigen

Figure 1:
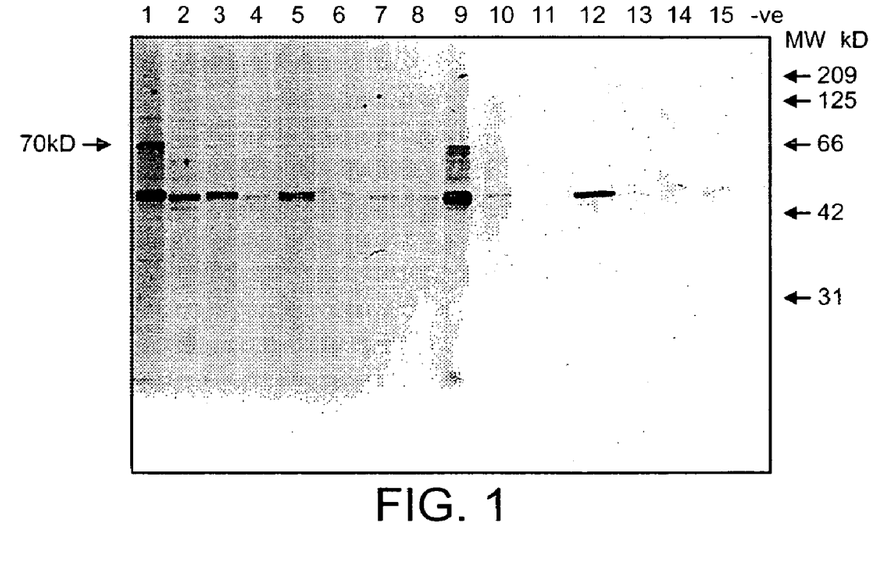
FIG. 1 is a Western Blot showing six rheumatoid sera (lanes 1–6), five normal sera (lanes 7–11) and four disease controls (lanes 12–15) reacting with chondrosarcoma lysates. Molecular weight markers are shown.

When RA and control sera were blotted against chondrocyte extracts, 30% RA sera reacted with a 78 Kd protein compared to 10% of control sera (FIG. 1). Sequencing of three tryptic peptides by low energy CAD identified one component of the 78 D band as the 78 kD glucose-regulated protein, also known as immunoglobulin heavy chain binding protein (BiP). DNA sequence analysis of p78 from articular chondrocyte cDNA showed a number of deviations from the published sequence (accession number X87949). A total of six single nucleotide substitutions and a codon insertion result in three amino acid substitutions and an arginine insertion at position 834–836 of p78 (accession number AF188611).

Immunological Tests in Rheumatoid Arthritis

Figure 2:
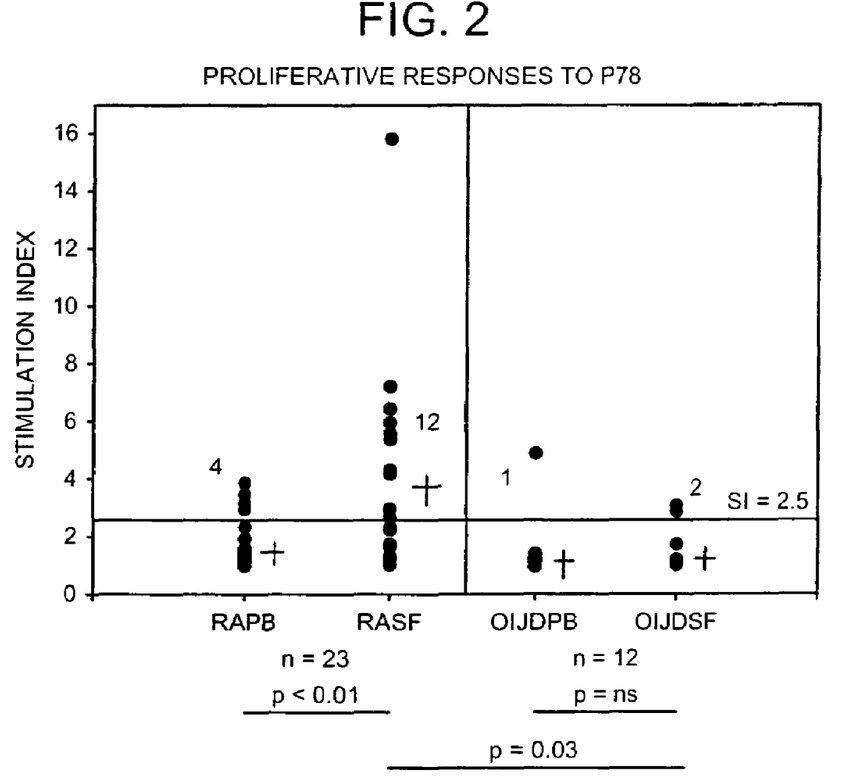
FIG. 2 is a graph depicting lymphocyte proliferation in mononuclear cells cultured for six days expressed as a stimulation index: (proliferation in the presence of p78)/(proliferation in the presence of culture medium alone). A stimulation value of 2.5 was considered significant. Abbreviations: RAPB=rheumatoid arthritis peripheral blood; RASF=rheumatoid arthritis synovial fluid; OIJDPB=other inflammatory joint diseases peripheral blood; OIJDSF=other inflammatory joint diseases synovial fluid.

T cell proliferative responses were determined for mononuclear cell preparations from paired peripheral blood and synovial fluid samples obtained from 23 patients with rheumatoid arthritis and from 12 disease controls. Twelve of 23 (52 percent) patients with RA and only 2 of 12 (17 percent) of disease controls showed increased synovial proliferation (FIG. 2). The prolifeative response to p78 of RA synovial T cells was significantly higher than that of the paired peripheral blood (stimulation index, mean±SEM: SF 3.5±0.7; PB 1.6±0.2; p<0.01 Wilcoxon paired test)). A significant difference was also seen between synovial fluid responses to p78 between RA patients and disease controls (SI: RA 3.5±0.7; OLID 1.4±0.2; p=0.03 Mann Whitney U test). There was no association with HLA-DR as 50% of responders and non-responders were HLA-DR4 positive (data not shown). Rheumatoid synovial fluid T cell proliferation to p78 was inhibited by 66–84% by anti-HLA-DR monoclonal antibody L243 (ATCC. Rocklille, Md.) (data not shown).

No IFNg could be measured in the supernatants from the paired synovial fluid and peripheral blood mononuclear cells (data not shown) despite using an ELISA sensitive to 0.01 ng/ml. No IFNg could be detected by intracellular fluorescence in the peripheral blood T cells of RA patients (n=7) or healthy controls (n=2) after stimulation by p78 (data not shown). These findings imply that the responding T cells were unlikely to belong to the classical IFNg producing TH1 subsets {1461}.

Immunological Studies in Experimental Arthritis

Induction of experimental arthritis with p78 Immunisation of DBA/1, C57BL mice and Lewis rats with p78 in Freund's complete adjuvant (CFA) did not lead to the development of arthritis (data not shown). There was a similar lack of arthritogenicity of p78 when injected with CFA into HLA-DR1$^{+/+}$ (0/10 mice) or into HLA-DR4$^{+/-}$(0/5) mice.

Immune Response to p78 in Experimental Arthritis

Figure 3:
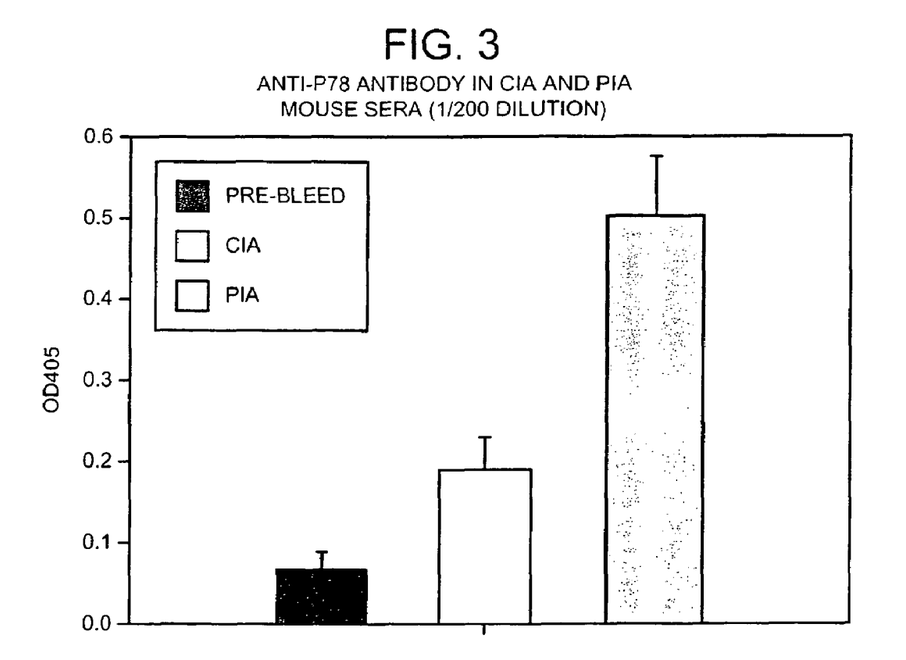
FIG. 3 is a bar chart depicting antibodies to recombinant human p78 in the sera of mice measured by ELISA and expressed as OD405. Shown are the values for the animals bled before the induction of experimental arthritis (prebleed), at the onset of collagen-induced arthritis (CIA), and of pristine-induced arthritis.

Despite the failure to induce arthritis by immunising animals with p78, we investigated whether DBA/1 mice during the course of CIA or PIA developed antibodies to p78. The results are depicted in FIG. 3. Mice developed serum anti-p78 antibodies at the onset CIA(O.D.$_{405}$ 0.189±0.042, m±sem) and PIA (0.504±0.074) when compared to pre-bleed sera (0.070±0.019; p<versus CIA and p<versus PIA, respectively). furthermore, the concentration of these antibodies was significantly higher in the PIA mice aa compared to the CIA mice. There were 14 mice in each group.

Prevention of Collagen-Induced Arthritis by Intravenous Administration of p78

The presence antibodies to p78 in the sera of mice with CIA or PIA suggested that manipulating the immune response to p78 might prevent the subsequent development of CIA by a bystander phenomenon. HLA-DR1$^{+/+}$ transgenic mice were injected intravenously with 1 mg of p78 prior to immunisation with type II collagen in CFA one week later (Table 2). Whereas 83% of animals had 46% of their limbs involved with arthritis at 8 weeks when pretreated with saline, only 10% of animals had only 3% of their limbs involved with arthritis in the group previously given intravenous p78. These differences are highly significant ($p \leq 0.008$ an $p \leq 0.0001$). Table 2 also shows that there was a significant reduction in anti-collagen antibodies in the p78 pre-treated animals to one third the level in the controls. The reduction was equal in the IgG1 and IgG2 isotypes (Table 3). The histology of the joints of these animals confirmed the clinical findings in that there was no synovitis in the joints of pre-treated mice.

We have shown in this study that 30% of patients with RA have antibodies, detected by Western blotting, directed against the human chaperonin BiP/GRP78, and named by us p78. Furthermore, T cells from the rheumatoid synovial fluid proliferated preferentially to p78. There was minimal response by the T cells from the peripheral blood of the same patients. The T cells from patients with other inflammatory arthritides, whether from the synovial fluid or the peripheral blood, did not significantly proliferate to p78. Finally, the proliferative response was inhibited by anti-HLA-DR monoclonal antibody suggesting that CD4+ positive T cells are responding to antigenic peptides presented in the context of HLA-DR. This polyclonal T cell response was not HLA-DR4 restricted. Thus p78 stimulation of T cell proliferation possesses two characteristics to be expected of a rheumatoid autoantigen, namely, it is joint and disease specific.

On the basis of these observations, we then undertook intravenous immunisation of mice with p78 in order to test the hypothesis that deviating the immune response to p78 would prevent the development of CIA by a bystander mechanism. This indeed proved to be the case with almost total prophylaxis against the induction of CIA in HLA-DR1$^{+/+}$ transgenic mice. In the past, various types of experimental arthritis have been prevented or treated by administration of bacterial, and especially mycobacterial, heat shock proteins such as HSP60 or T cells responding to whole HSP60 or to specific peptides {2103, 2280,2282,2283,2284, 2281}. However, it is of some importance to note that self-HSP60 peptides show no such protective effects {2281}. Thus the ability of p78 to prevent CIA is of fundamental importance. The observations described in this work are the first, to our knowledge, which implicate an endogenous chaperone in the pathogenesis of RA and the immunotherapy of experimental arthritis. The potential for the immunotherapy of RA is clearly apparent.

2. Use of Tests for Detection of Antibodies to p78 in Biological Fluids or Culture Supernatants Several techniques can be used, such as agglutination, Western blotting, and ELISA.

ELISA Protocol for the Detection of Antibodies to p78 in Sera

ELISA plates are coated half with p78 in bicarbonate buffer and half with bicarbonate buffer alone for 4 hours at room temperature. After 2 washes in PBS the plate is blocked for 2 hours at room temperature with 10% goat serum in PBS with 0.05% Tween 20 to stop non-specific binding of protein. After 2 further washes diluted sera (in PBS/1% goat serum/0.05% Tween) is added in duplicate to both the p78 coated and non-coated sides of the plate. After 4 washes biotin conjugated anti human immunoglobulin (1/10000 diluted in PBS/1% goat serum/0.05% Tween)) is added to the plate. The plate is washed 6 times. Bound biotinylated antibody is detected with streptavidin conjugated horse-radish peroxidase (1/800 in PBS/1% goat serum/ 0.05% Tween) and suitable substrate. Sera containing antibodies to p78 are determined spectrophotometrically. This test forms the basis of a diagnostic and/or prognostic test for rheumatoid arthritis.

3. Therapeutic Application

Many routes of administration of the recombinant protein or vector are possible, including intravenous, intramuscular, nasal, oral, cutaneous, and topical. There are several approaches to using p78 or derivatives for therapeutic purposes, including the following:

(a) Induction of Mucosal Tolerance

Delivery of p78 autoantigen or peptides derived therefrom by mucosal routes, e.g. through the intestine or nasal mucosa, alters the immune response by downregulating disease activity leaving the patient's immune system otherwise intact. Alternatively p78 or p78 peptides can be delivered as DNA plasmids encoding them with an appropriate mammalian expression vector.

(b) Vaccination with TCR Peptides

Peptides of the CDR3 region of the T cell receptor Valpha and Vbeta chains can be synthesised and used as vaccines for delivery by intradermal or intramuscular injection. Plasmids encoding these peptides can be used in the same way.

(c) MHC Blockade with Native or Altered Peptides

The p78 peptides may be given parenterally or orally in appropriate cases either unmodified or modified by amino acid substitution and/or attachment of chemical groupings so as to block MHC and especially HLA-DR4 thereby leading to suppression of T cell activation and disease. P78 peptides either native or altered may be combined with soluble HLA-DR4 molecules and applied parenterally or orally.

(d) Induction of Tolerance by Plasmid DNA Immunisation

Plasmids consisting of DNA coding for whole p78 protein or its peptides linked to a mammalian expression vector may be given by injection. DNA coding for human IL-10, IL-4, IL-11, or TGF-beta, incorporated singly or in any combination, may be used to deviate the immune response to p78 towards a TH2 mode so as to suppress disease.

In the therapeutic regimes indicated above the protein or derived peptide may be administered in appropriate compositions delivering amounts ranging from about 0.1 micrograms to about 1 gram or the equivalent in the case of plasmid or vaccine preparations.

TABLE 1

Prevention of CIA by intravenous injection of recombinant p78

| Tolerogen[a] | % Arthritic Mice at 8 weeks[b] | % Arthritic Limbs at 8 weeks[b] | Antibodies (IgG) to CII[c] |
|---|---|---|---|
| p78 (1 mg) | 1/10 (10%)* | 1/40 (3%)** | 22 ± 9*** |
| PBS | 5/6 (83%) | 11/24 (46%) | 68 ± 10 |

[a]HLA-DR[+/+] transgenic mice were injected intravenously with either PBS (negative control) or recombinant p78. Either 1 mg of protein dissolved in 0.1 ml of PBS or 0.1 ml of PBS was administered intravenously and mice were immunised with type II collagen in CFA seven days after the intravenous dose.
[b]The incidence of arthritis is reported at 8 weeks after immunisation.
[c]Antibodies represent mean units per group using sera collected 8 weeks after immunisation. ELISAs were performed and results are reported as units of aactivity derived by cmparison of test sera with the standard serum which was arbitrarily defined as having 50 units of acitivity. Sera were analysed individually and results shown as the mean ± SD for each group of animals.
*p $\leq$ 0.008 (Fischer's Exact test)  $\leq$ 0.0001 (Fischer's Exact test) * <0.05 (Students t test)

TABLE 2

IgG1 and IgG2 antibody isotypes to type II collagen in mice treated intravenously with either recombinant p78 or PBS.

| Tolerogen[a] | IgG1 antibodies to type II collagen[b] | IgG2 antibodies to type II collagen[b] |
|---|---|---|
| p78 (1000 μg) | 0.71 ± 0.019* | 0.110 ± 0.022* |
| PBS | 0.135 ± 0.066 | 0.250 ± 0.044 |

[a]HLA-DR1 transgenic mice were injected intravenously with either PBS (negative control) or recombinant p78 followed by immunisation with collagen type II in CFA one week later.
[b]ELISAs were performed as described in caption to Table 2.
*p <0.05 (Students t test)

TABLE 3

Anti-p78 antibody in CIA or PIA mouse sera (1:200 dil)

| Mouse ID | Subtract blanks and non-coated values Prebleed | CIA onset | PIA (mouse ID #1–14) |
|---|---|---|---|
| 961 | 0.000 | 0.243 | 0.263 |
| 982 | 0.181 | 0.328 | 0.981 |
| 963 | 0.155 | 0.567 | 0.780 |
| 965 | 0.076 | 0.198 | 0.934 |
| 966 | 0.162 | 0.257 | 0.388 |
| 967 | 0.068 | 0.000 | 0.291 |
| 968 | 0.039 | 0.189 | 0.469 |
| 970 | 0.000 | 0.000 | 0.551 |
| 197 | 0.173 | 0.000 | 0.537 |
| 198 | 0.023 | 0.000 | 0.711 |
| 200 | 0.000 | 0.099 | 0.430 |
| 248 | 0.000 | 0.183 | 0.535 |
| 702 | 0.090 | 0.011 | 0.038 |
| 703 | 0.012 | 0.206 | 0.147 |
| 705 | | 0.341 | |
| 706 | | 0.407 | |
| Mean | 0.070 | 0.189 | 0.504 |
| Count | 14 | 16 | 14 |
| SEM | 0.019 | 0.042 | 0.074 |

LEGENDS TO FIGURES

FIG. 1

Western blotting showing 6 rheumatoid sera (lanes 1–6), 5 normal sera (lanes 7–11) and 4 disease controls (lanes 12–15) reacting with chondrosarcoma lysate. Molecular weight markers are shown.

FIG. 2

Lymphocyte proliferation in mononuclear cells cultured for 6 days expressed as a stimulation index: proliferation in the presence of p78/proliferation in the presence of culture medium alone. A stimulation of $\geq 2.5$ was considered significant. RAPB, rheumatoid arthritis peripheral blood; RASF, rheumatoid arthritis synovial fluid; OIJDPB, other inflammatory joint diseases peripheral blood; OIJDSF, other inflammatory joint diseases synovial fluid.

FIG. 3

Antibodies to recombinant human p78 in the sera of mice measured by ELISA and expressed as $OD_{405}$. Shown are the values for the animals bled before the induction of experimental arthritis pre-bleed), and at the onset of collagen-induced arthritis (CIA) and of pristane-induced arthritis (PIA).

REFERENCES

Bibliography

1. Gregersen P K, Silver J, Winchester R J. The shared epitope hypothesis. An approach to understanding the molecular genetics of susceptibility to rheumatoid arthritis. Arthritis Rheum. 1987; 30: 1205–1213.
2, Panayi G S. T cell dependent pathways in rheumatoid arthritis. Current Opinion in Rheumatology 1997; 9: 236–240.
3. Sakata A, Sakata K, Ping H, Ohmura T, Tsukano M, Kakimoto K. Successful induction of severe destrictive arthritis by the transfer of in vitro activated synovial fluid T cells from patients with rheumatoid arthritis (RA) in severe combined immunodeficient (SCID) mice. Clin Exp Immunol 1996; 104: 247–254.

4. Ikeda Y, Masuko K, Nakai Y, et al. High frequencies of identical T cell clonotypes in synovial tissues of rheumatoid arthritis patients suggest the occurrence of common antigen-driven immune responses. Arthritis & Rheumatism 1996; 39: 446–453, 5. Uematsu Y, Wege H, Strauss A, et al. The T cell receptor repertoire in the synovial fluid of a patient with rheumatoid arthritis is polyclonal. Proc Natl Acad Sci 1991; 88: 8534–8538.

6. Cope A P, Sonderstrup G. Evaluating candidate autoantigens in rheumatoid arthritis. Springer Seminars in Immunology 1998; 20: 23–39.

7. Laine V a. Early synovectomy in rheumatoid arthritis. [Review] [87 refs]. Annual Review of Medicine 1967; 18: 173–184.

8. Laskin R S. Total condylar knee replacement in patients who have rheumatoid arthritis. A ten year follow-up study. J Bone Jt Surg (Am) 1991; 72: 529–535.

9. Laemmli U K. Cleavage of structural proteins during the assembly of the head of bacteriophage T4. Nature 1970; 227: 680–685.

10. Towbin H, Staehelin T, Gordon T. Electrophoretic transfer of proteins from SDS and acid/urea gels to nitrocellulose. Proc Nat Acad Sci 1979; 76: 4350

11. Jobanputra P, Corrigall V, Panayi GS. Expression of the 65 kD heat shock protein in human chodrocytes. Brit J Rheumatol 1993; 32: 259–230.

12. Bunce M, O'Neill C M, Barnado MCNM, et al. Phototyping:comprehensive DNA typing for HLA-A, B, C, DRB3, DRB5 and DQBI by PCR with 144 primer mixes utilising sequence-specific primers (PCR-SSP). Tissue Antigens 1995; 46: 355–367.

14. Mossman T R, Cherwinski H. Bond MW, Giedlin Mass., Coffman R L. two types of murine T helper T cell clones 1 definition according to profiles of lymphokine activities and secreted proteins. J Immunol 1986; 136: 2348–2356.

15. Auger I, Roudier J. A function for the QKRAA amina acid motif: mediating binding of DnaJ to DnaK. Implications for the Association of Rheumatoid Arthritis with HLA-DR4. J Clin Invest 1997, 99: 1818–1822.

16. van Shooten WCA, Devereux D, Ho CH, Aguilar BA, Rust CJJ. Joint derived T cells in rheumatoid arthritis react with self-immunoglobulin heavy chains or immunoglobulin binding proteins that copurify with immunoglobulin. Eur J Immunol 1945; 23: 93–98.

17. Knarr G, Gething M, Modrow S, Buchner J. BiP binding sequences in antibodies. J Bio Chem 1995; 46: 27589–27594.

18. Winfield J B. Stress proteins, arthritis and autoimmunity. Arthritis & Rheum 1989; 32: 1497–1504.

19. Srivastava P K, Menoret A, Basu S, Binder R J, McQuade K L. Heat shock proteins come of age: Primitive functions acquire new roles in an adaptive world. Immunity 1998; 8: 657–665.

20. Arnold-Schild D, Hanau D, Spehner D, et al. Cutting Edge: receptor-mediated endocytosis of heat shock proteins by professional anigen-presenting cells. J Immunol 1999; 162: 3757–3760.

22. Blass S, Burmester G. Anti-BiP antibodies in rheumatoid arthritis: method and test kits for detecting them. 1999; WO 99/18131: (Abstract)

23. Rosloniec E F, Brand DD, Myers L K, et al. Induction of autoimmune arthritis in HLA-DR4 (DRB1*0401) transgenic mice by immunization with human and bovine type II collagen. J Immunol 1998; 160: 2573–2578.

24. Myers L K, Rosloniec E F, Cremer Mass., Kang A H. Collagen-induced arthritis, an animal model of autoimmunity. [Review] [144 refs]. Life Sciences 1997; 61: 1861–1878.

25. Wooley P H, Sud S, Whalen J D, Nasser S. Pristane-induced arthritis in mice. V. Susceptibility to pristane-induced arthritis is determined by the genetic regulation of the T cell repertoire. Arthritis & Rheumatism 1998; 41: 2022–2031.

26. Kouskoff V, Korganow A, Duchatelle V, Degott C, Benoist C, Mathis D. Organ-specific disease provoked by systemic autoimmunity. Cell 1996; 67: 811–822.

27. Verheijden G F, Rijnders A W, Bos E, et al. Human cartilage glycoprotein-39 as a candidate autoantigen in rheumatoid arthritis. Arthritis & Rheumatism 1997; 40: 1115–

28. Low-Friedrich I, Weisensee D, Mitrou P, Schoeppe W. Cytokines induce stress protein formation in cultured cardiac myocytes. Basic Research in Cardiology 1992; 87: 12–18.

29. Haskins K, Wegmann D. Diabetogenic T-cell clones. [Review] [49 refs]. Diabetes 1996; 45: 1299–1305.

30. Hirvonen MR. Brune B, Lapetina E G. Heat shock proteins and macrophage resistance to the toxic effects of nitric oxide. Biochemical Journal 1996; 315: 845–849.

31. Beech J T, Siew L K, Ghoraishian M, Stasiuk L M, Elson C J, Thompson S J. CD4+ TH2 cells specific for mycobacterial 65-kilodalton heat shock protein protect against pristane-induced arthritis. J Immunol 1997; 159: 3692–3697.

32. van Eden W, Thole J E, van der Zee R, et al. Cloning of the mycobacterial epitope recognized by T lymphocytes in adjuvant arthritis. Nature 1988; 331: 171–173.

33. van den Broek M F, Hogervorst E J, van, et al. Protection against streptococcal cell wall-induced arthritis by pretreatment with the 65-kD mycobacterial heat shock protein. J Exp Med 1989; 170: 449–466.

34. Thompson S J, Rook G A, Brealey R J, van, der Zee R, Elson C J. Autoimmune reactions to heat-shock proteins in pristane-induced arthritis. Eur J Immunol 1990; 20: 2479–2484.

35. Billingham M e., Carney S, Butler R, Colston M J. A mycobacterial 65-kD heat shock protein induces antigen-specific suppression of adjuvant arthritis, but is not itself arthritogenic. J Exp Med 1990; 171: 339–344.

36. Anderton S M, van der, Zee R, et al. Activation of T cells recognizing self 60-kD heat shock protein can protect against experimental arthritis. J Exp Med 1995; 181: 943–952.

What is claimed is:

1. A recombinant immunoglobulin heavy chain binding protein designated BiP(GRP78) and having an amino acid sequence as shown in SEQ. ID. NO: 1 or SEQ. ID. NO: 2.

2. A pharmaceutical composition for the treatment of rheumatoid arthritis in mammals, including humans, the composition comprising an anti-rheumatoid-arthritic amount of an isolated immunoglobulin heavy chain binding protein designated BiP(GRP78), and having an amino acid sequence as shown in SEQ. ID. NO: 1 or SEQ. ID. NO: 2, in combination with a pharmaceutically-suitable carrier.

3. The pharmaceutical composition of claim 2, wherein the immunoglobulin heavy chain binding protein is a recombinant immunoglobulin heavy chain binding protein.

4. A method for treating rheumatoid arthritis in a mammalian subject in need thereof, including a human subject, the method comprising administering to the subject an anti-rheumatoid-arthritic amount of a recombinant immunoglobulin heavy chain binding protein having an amino acid sequence as shown in SEQ. ID. NO: 1 or SEQ. ID NO: 2.

5. The method of claim 4, wherein the immunoglobulin heavy chain binding protein is administered orally, nasally, subcutaneously, or intravenously.

6. A method for diagnosing the presence of rheumatoid arthritis in a mammalian subject, including a human subject, the method comprising contacting a bodily fluid from the subject selected from the group consisting of whole blood, blood plasma, blood serum, saliva, mucus, synovial fluid, and cerebrospinal fluid, to an immunoglobulin heavy chain binding protein, wherein the bodily fluid is contacted with an immunoglobulin heavy chain binding protein having an amino acid sequence as shown in SEQ. ID. NO: 1 or SEQ. ID. NO: 2, and then ascertaining the presence or absence of anti-immunoglobulin heavy chain binding protein antibodies in the bodily fluid tested, the presence of antibodies indicating the presence of rheumatoid arthritis in the subject.

7. The method of claim 6, wherein the presence of an anti-immunoglobulin heavy chain binding protein antibodies is ascertained using an enzyme-linked immunosorbent assay (ELISA) incorporating an immunoglobulin heavy chain binding protein.

8. A kit for diagnosing the presence of rheumatoid arthritis in a mammalian subject, including a human subject, the kit comprising:

an amount of an isolated immunoglobulin heavy chain binding protein designated BiP(GRP78), and having an amino acid sequence as shown in SEQ. ID. NO: 1 or SEQ. ID. NO: 2, disposed in a suitable container.

9. The kit of claim 8, further comprising instructions for use of the kit.

10. The kit of claim 8, comprising a recombinant immunoglobulin heavy chain binding protein.

11. The kit of claim 8, comprising an enzyme-linked immunosorbent assay that incorporates the immunoglobulin heavy chain binding protein.

12. The kit of claim 11, comprising a recombinant immunoglobulin heavy chain binding protein.

13. The kit of claim 8, comprising a Western Blot assay that incorporates the immunoglobulin heavy chain binding protein.

14. The kit of claim 13, comprising a recombinant immunoglobulin heavy chain binding protein.

15. An isolated polypeptide having an amino acid sequence as shown in SEQ. ID. NO: 1 or SEQ. ID. NO: 2.

* * * * *

SEQUENCE LISTING

<160> NUMBER OF SEQ ID NOS: 9

<210> SEQ ID NO 1
<211> LENGTH: 639
<212> TYPE: PRT
<213> ORGANISM: Homo sapiens

<400> SEQUENCE: 1

```
Met Glu Glu Asp Lys Lys Glu Asp Val Gly Thr Val Val Gly Ile Asp
1               5                   10                  15

Leu Gly Thr Thr Tyr Ser Cys Val Gly Val Phe Lys Asn Gly Arg Val
                20                  25                  30

Glu Ile Ile Ala Asn Asp Gln Gly Asn Arg Ile Thr Pro Ser Tyr Val
            35                  40                  45

Ala Phe Thr Pro Glu Gly Glu Arg Leu Ile Gly Asp Ala Ala Lys Asn
        50                  55                  60

Gln Leu Thr Ser Asn Pro Glu Asn Thr Val Phe Asp Ala Lys Arg Leu
65                  70                  75                  80

Ile Gly Arg Thr Trp Asn Asp Pro Ser Val Gln Gln Asp Ile Lys Phe
                85                  90                  95

Leu Pro Phe Lys Val Val Glu Lys Lys Thr Lys Pro Tyr Ile Gln Val
                100                 105                 110

Asp Ile Gly Gly Gly Gln Thr Lys Thr Phe Ala Pro Glu Glu Ile Ser
            115                 120                 125

Ala Met Val Leu Thr Lys Met Lys Glu Thr Ala Glu Ala Tyr Leu Gly
        130                 135                 140

Lys Lys Val Thr His Ala Val Val Thr Val Pro Ala Tyr Phe Asn Asp
145                 150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ala Ile Ala Tyr Gly
                180                 185                 190

Leu Asp Lys Arg Glu Gly Glu Lys Asn Ile Leu Val Phe Asp Leu Gly
            195                 200                 205

Gly Gly Thr Phe Asp Val Ser Leu Leu Thr Ile Asp Asn Gly Val Phe
        210                 215                 220

Glu Val Val Ala Thr Asn Gly Asp Thr His Leu Gly Gly Glu Asp Phe
225                 230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
                260                 265                 270

Glu Val Glu Lys Ala Lys Arg Ala Leu Ser Ser Gln His Gln Ala Arg
            275                 280                 285

Ile Glu Ile Glu Ser Phe Tyr Glu Gly Glu Asp Phe Ser Glu Thr Leu
        290                 295                 300

Thr Arg Ala Lys Phe Glu Leu Asn Met Asp Leu Phe Arg Ser Thr
305                 310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
                340                 345                 350

Ile Gln Gln Leu Val Lys Glu Phe Phe Asn Gly Lys Glu Pro Ser Arg
```

-continued

```
                355                 360                 365
Gly Ile Asn Pro Asp Glu Ala Val Ala Tyr Gly Ala Val Gln Ala
    370                 375                 380
Gly Val Leu Ser Gly Asp Gln Asp Thr Gly Asp Leu Val Leu Leu Asp
385                 390                 395                 400
Val Cys Pro Leu Thr Leu Gly Ile Glu Thr Val Gly Gly Val Met Thr
                405                 410                 415
Lys Leu Ile Pro Arg Asn Thr Val Pro Thr Lys Ser Gln Ile
                420                 425                 430
Phe Ser Thr Ala Ser Asp Asn Gln Pro Thr Val Thr Ile Lys Val Tyr
                435                 440                 445
Glu Gly Glu Arg Pro Leu Thr Lys Asp Asn His Leu Leu Gly Thr Phe
    450                 455                 460
Asp Leu Thr Gly Ile Pro Pro Ala Pro Arg Gly Val Pro Gln Ile Glu
465                 470                 475                 480
Val Thr Phe Glu Ile Asp Val Asn Gly Ile Leu Arg Val Thr Ala Glu
                485                 490                 495
Asp Lys Gly Thr Gly Asn Lys Asn Lys Ile Thr Ile Thr Asn Asp Gln
                500                 505                 510
Asn Arg Leu Thr Pro Glu Glu Ile Glu Arg Met Val Asn Asp Ala Glu
                515                 520                 525
Lys Phe Ala Glu Glu Asp Lys Lys Leu Lys Glu Arg Ile Asp Thr Arg
    530                 535                 540
Asn Glu Leu Glu Ser Tyr Ala Tyr Ser Leu Lys Asn Gln Ile Gly Asp
545                 550                 555                 560
Lys Glu Lys Leu Gly Gly Lys Leu Ser Ser Glu Asp Lys Glu Thr Met
                565                 570                 575
Glu Lys Ala Val Glu Glu Lys Ile Glu Trp Leu Glu Ser His Gln Asp
                580                 585                 590
Ala Asp Ile Glu Asp Phe Lys Ala Lys Lys Glu Leu Glu Glu Ile
                595                 600                 605
Val Gln Pro Ile Ile Ser Lys Leu Tyr Gly Ser Ala Gly Pro Pro Pro
    610                 615                 620
Thr Gly Glu Glu Asp Thr Ala Glu Leu His His His His His His
625                 630                 635

<210> SEQ ID NO 2
<211> LENGTH: 633
<212> TYPE: PRT
<213> ORGANISM: Homo sapiens

<400> SEQUENCE: 2

Met Glu Glu Asp Lys Lys Glu Asp Val Gly Thr Val Val Gly Ile Asp
1               5                   10                  15
Leu Gly Thr Thr Tyr Ser Cys Val Gly Val Phe Lys Asn Gly Arg Val
                20                  25                  30
Glu Ile Ile Ala Asn Asp Gln Gly Asn Arg Ile Thr Pro Ser Tyr Val
            35                  40                  45
Ala Phe Thr Pro Glu Gly Glu Arg Leu Ile Gly Asp Ala Ala Lys Asn
    50                  55                  60
Gln Leu Thr Ser Asn Pro Glu Asn Thr Val Phe Asp Ala Lys Arg Leu
65                  70                  75                  80
Ile Gly Arg Thr Trp Asn Asp Pro Ser Val Gln Gln Asp Ile Lys Phe
                85                  90                  95
```

-continued

Leu Pro Phe Lys Val Glu Lys Lys Thr Lys Pro Tyr Ile Gln Val
            100                 105             110

Asp Ile Gly Gly Gln Thr Lys Thr Phe Ala Pro Glu Glu Ile Ser
            115                 120             125

Ala Met Val Leu Thr Lys Met Lys Glu Thr Ala Glu Ala Tyr Leu Gly
            130                 135             140

Lys Lys Val Thr His Ala Val Val Thr Val Pro Ala Tyr Phe Asn Asp
145             150                 155                 160

Ala Gln Arg Gln Ala Thr Lys Asp Ala Gly Thr Ile Ala Gly Leu Asn
                165                 170                 175

Val Met Arg Ile Ile Asn Glu Pro Thr Ala Ala Ile Ala Tyr Gly
            180                 185                 190

Leu Asp Lys Arg Glu Gly Glu Lys Asn Ile Leu Val Phe Asp Leu Gly
            195                 200                 205

Gly Gly Thr Phe Asp Val Ser Leu Leu Thr Ile Asp Asn Gly Val Phe
            210                 215                 220

Glu Val Val Ala Thr Asn Gly Asp Thr His Leu Gly Gly Glu Asp Phe
225             230                 235                 240

Asp Gln Arg Val Met Glu His Phe Ile Lys Leu Tyr Lys Lys Lys Thr
                245                 250                 255

Gly Lys Asp Val Arg Lys Asp Asn Arg Ala Val Gln Lys Leu Arg Arg
            260                 265                 270

Glu Val Glu Lys Ala Lys Arg Ala Leu Ser Ser Gln His Gln Ala Arg
            275                 280                 285

Ile Glu Ile Glu Ser Phe Tyr Glu Gly Glu Asp Phe Ser Glu Thr Leu
            290                 295                 300

Thr Arg Ala Lys Phe Glu Glu Leu Asn Met Asp Leu Phe Arg Ser Thr
305             310                 315                 320

Met Lys Pro Val Gln Lys Val Leu Glu Asp Ser Asp Leu Lys Lys Ser
                325                 330                 335

Asp Ile Asp Glu Ile Val Leu Val Gly Gly Ser Thr Arg Ile Pro Lys
            340                 345                 350

Ile Gln Gln Leu Val Lys Glu Phe Phe Asn Gly Lys Glu Pro Ser Arg
            355                 360                 365

Gly Ile Asn Pro Asp Glu Ala Val Ala Tyr Gly Ala Ala Val Gln Ala
            370                 375                 380

Gly Val Leu Ser Gly Asp Gln Asp Thr Gly Asp Leu Val Leu Leu Asp
385             390                 395                 400

Val Cys Pro Leu Thr Leu Gly Ile Glu Thr Val Gly Gly Val Met Thr
                405                 410                 415

Lys Leu Ile Pro Arg Asn Thr Val Pro Thr Lys Lys Ser Gln Ile
            420                 425                 430

Phe Ser Thr Ala Ser Asp Asn Gln Pro Thr Val Thr Ile Lys Val Tyr
                435                 440                 445

Glu Gly Glu Arg Pro Leu Thr Lys Asp Asn His Leu Leu Gly Thr Phe
            450                 455                 460

Asp Leu Thr Gly Ile Pro Pro Ala Pro Arg Gly Val Pro Gln Ile Glu
465             470                 475                 480

Val Thr Phe Glu Ile Asp Val Asn Gly Ile Leu Arg Val Thr Ala Glu
                485                 490                 495

Asp Lys Gly Thr Gly Asn Lys Asn Lys Ile Thr Ile Thr Asn Asp Gln
            500                 505                 510

Asn Arg Leu Thr Pro Glu Glu Ile Glu Arg Met Val Asn Asp Ala Glu

```
                515                 520                 525
Lys Phe Ala Glu Glu Asp Lys Lys Leu Lys Glu Arg Ile Asp Thr Arg
    530                 535                 540

Asn Glu Leu Glu Ser Tyr Ala Tyr Ser Leu Lys Asn Gln Ile Gly Asp
545                 550                 555                 560

Lys Glu Lys Leu Gly Gly Lys Leu Ser Ser Glu Asp Lys Glu Thr Met
                565                 570                 575

Glu Lys Ala Val Glu Lys Ile Glu Trp Leu Glu Ser His Gln Asp
            580                 585                 590

Ala Asp Ile Glu Asp Phe Lys Ala Lys Lys Glu Leu Glu Glu Ile
        595                 600                 605

Val Gln Pro Ile Ile Ser Lys Leu Tyr Gly Ser Ala Gly Pro Pro Pro
    610                 615                 620

Thr Gly Glu Glu Asp Thr Ala Glu Leu
625                 630
```

<210> SEQ ID NO 3
<211> LENGTH: 1917
<212> TYPE: DNA
<213> ORGANISM: Homo sapiens

<400> SEQUENCE: 3

```
atggaggagg acaagaagga ggacgtgggc acggtggtcg gcatcgacct ggggaccacc     60
tactcctgcg tcggcgtgtt caagaacggc cgcgtggaga tcatcgccaa cgatcagggc    120
aaccgcatca cgccgtccta tgtcgccttc actcctgaag ggaacgtctc gattggcgat    180
gccgccaaga accagctcac ctccaacccc gagaacacgg tctttgacgc caagcggctc    240
atcggccgca cgtggaatga cccgtctgtg cagcaggaca tcaagttctt gccgttcaag    300
gtggttgaaa agaaaactaa accatacatt caagttgata ttggaggtgg gcaaacaaag    360
acatttgctc ctgaagaaat ttctgccatg gttctcacta aaatgaaaga aaccgctgag    420
gcttatttgg gaagaaggt tacccatgca gttgttactg taccagccta ttttaatgat    480
gcccaacgcc aagcaaccaa agacgctgga actattgctg gcctaaatgt tatgaggatc    540
atcaacgagc tacggcagc tgctattgct tatggcctgg ataagaggga ggggagaag    600
aacatcctgg tgtttgacct gggtggcgga accttcgatg tgtctcttct caccattgac    660
aatggtgtct tcgaagttgt ggccactaat ggagatactc atctggtgg agaagacttt    720
gaccagcgtg tcatggaaca cttcatcaaa ctgtacaaaa agaagacggg caaagatgtc    780
aggaaagaca atagagctgt gcagaaactc cggcgcgagg tagaaaaggc caaacgggcc    840
ctgtcttctc agcatcaagc aagaattgaa attgagtcct ctatgaagg agaagacttt    900
tctgagaccc tgactcgggc caaatttgaa gagctcaaca tggatctgtt ccggtctact    960
atgaagcccg tccagaaagt gttggaagat tctgatttga agaagtctga tattgatgaa   1020
attgttcttg ttggtggctc gactcgaatt ccaaagattc agcaactggt taaagagttc   1080
ttcaatggca aggaaccatc ccgtggcata aacccagatg aagctgtagc gtatggtgct   1140
gctgtccagg ctggtgtgct ctctggtgat caagatacag gtgacctggt actgcttgat   1200
gtatgtcccc ttacacttgg tattgaaact gtgggaggtg tcatgaccaa actgattcca   1260
aggaacacag tggtgcctac caagaagtct cagatctttt ctacagcttc tgataatcaa   1320
ccaactgtta caatcaaggt ctatgaaggt gaaagacccc tgacaaaaga caatcatctt   1380
ctgggtacat ttgatctgac tggaattcct cctgctcctc gtgggggtccc acagattgaa   1440
```

-continued

```
gtcacctttg agatagatgt gaatggtatt cttcgagtga cagctgaaga caagggtaca    1500
gggaacaaaa ataagatcac aatcaccaat gaccagaatc gcctgacacc tgaagaaatc    1560
gaaaggatgg ttaatgatgc tgagaagttt gctgaggaag acaaaaagct caaggagcgc    1620
attgatacta gaaatgagtt ggaaagctat gcctattctc taaagaatca gattggagat    1680
aaagaaaagc tgggaggtaa actttcctct gaagataagg agaccatgga aaaagctgta    1740
gaagaaaaga ttgaatggct ggaaagccac caagatgctg acattgaaga cttcaaagct    1800
aagaagaagg aactggaaga aattgttcaa ccaattatca gcaaactcta tggaagtgca    1860
ggccctcccc caactggtga agaggataca gcagaactcc accaccacca ccaccac      1917
```

<210> SEQ ID NO 4
<211> LENGTH: 32
<212> TYPE: DNA
<213> ORGANISM: Artificial sequence
<220> FEATURE:
<223> OTHER INFORMATION: Primer

<400> SEQUENCE: 4
tatacatatg gaggaggaca agaaggagga cg                                   32

<210> SEQ ID NO 5
<211> LENGTH: 32
<212> TYPE: DNA
<213> ORGANISM: Artificial sequence
<220> FEATURE:
<223> OTHER INFORMATION: Primer

<400> SEQUENCE: 5
ccacctcgag ttctgctgta tcctcttcac ca                                   32

<210> SEQ ID NO 6
<211> LENGTH: 15
<212> TYPE: PRT
<213> ORGANISM: Artificial sequence
<220> FEATURE:
<223> OTHER INFORMATION: Isolated peptide fragment

<400> SEQUENCE: 6

Asn Gln Leu Thr Ser Asn Pro Glu Asn Thr Val Phe Asp Ala Lys
1               5                   10                  15

<210> SEQ ID NO 7
<211> LENGTH: 14
<212> TYPE: PRT
<213> ORGANISM: Artificial sequence
<220> FEATURE:
<223> OTHER INFORMATION: Isolated peptide fragment

<400> SEQUENCE: 7

Ser Asp Ile Asp Glu Ile Val Leu Val Gly Gly Ser Thr Arg
1               5                   10

<210> SEQ ID NO 8
<211> LENGTH: 12
<212> TYPE: PRT
<213> ORGANISM: Artificial sequence
<220> FEATURE:
<223> OTHER INFORMATION: Isolated peptide fragment

<400> SEQUENCE: 8

Thr Trp Asn Asp Pro Ser Val Gln Gln Asp Ile Lys
1               5                   10

<210> SEQ ID NO 9
<211> LENGTH: 2554
<212> TYPE: DNA
<213> ORGANISM: Homo sapiens

<400> SEQUENCE: 9

```
aggtcgacgc cggccaagac agcacagaca gattgaccta ttggggtgtt tcgcgagtgt      60
gagagggaag cgccgcggcc tgtatttcta gacctgccct tcgcctggtt cgtggcgcct     120
tgtgaccccg ggcccctgcc gcctgcaagt cggaaattgc gctgtgctcc tgtgctacgg     180
cctgtggctg gactgcctgc tgctgcccaa ctggctggca agatgaagct ctccctggtg     240
gccgcgatgc tgctgctgct cagcgcggcg cgggccgagg aggaggacaa gaaggaggac     300
gtgggcacgg tggtcggcat cgacttgggg accacctact cctgcgtcgg cgtgttcaag     360
aacggccgcg tggagatcat cgccaacgat cagggcaacc gcatcacgcc gtcctatgtc     420
gccttcactc ctgaagggga acgtctgatt ggcgatgccg ccaagaacca gctcacctcc     480
aaccccgaga cacggtcttt gacgccaag cggctcatcg ccgcacgtg aatgacccg     540
tctgtgcagc aggacatcaa gttcttgccg ttcaaggtgg ttgaaaagaa aactaaacca     600
tacattcaag ttgatattgg aggtgggcaa acaaagacat ttgctcctga gaaatttct     660
gccatggttc tcactaaaat gaaagaaacc gctgaggctt atttgggaaa gaaggttacc     720
catgcagttg ttactgtacc agcctatttt aatgatgccc aacgccaagc aaccaaagac     780
gctggaacta ttgctggcct aaatgttatg gaggatcatca acgagcctac ggcagctgct     840
attgcttatg gcctggataa gagggagggg gagaagaaca tcctggtgtt tgacctgggt     900
ggcggaacct tcgatgtgtc tcttctcacc attgacaatg gtgtcttcga agttgtggcc    960
actaatggag atactcatct gggtggagaa gactttgacc agcgtgtcat ggaacacttc    1020
atcaaactgt acaaaaagaa gacgggcaaa gatgtcagga aggacaatag agctgtgcag    1080
aaactccggc gcgaggtaga aaaggccaag gccctgtctt ctcagcatca gcaagaatt    1140
gaaattgagt ccttctatga aggagaagac ttttctgaga ccctgactcg ggccaaattt    1200
gaagagctca acatggatct gttccggtct actatgaagc ccgtccagaa agtgttggaa    1260
gattctgatt tgaagaagtc tgatattgat gaaattgttc ttgttggtgg ctcgactcga    1320
attccaaaga ttcagcaact ggttaaagag ttcttcaatg gcaaggaacc atcccgtggc    1380
ataaacccag atgaagctgt agcgtatggt gctgctgtcc aggctggtgt gctctctggt    1440
gatcaagata caggtgacct ggtactgctt catgtatgtc cccttacact tggtattgaa    1500
actgtaggag gtgtcatgac caaactgatt ccaagtaata cagtggtgcc taccaagaac    1560
tctcagatct tttctacagc ttctgataat caaccaactg ttacaatcaa ggtctatgaa    1620
ggtgaaagac ccctgacaaa agacaatcat cttctgggta catttgatct gactggaatt    1680
cctcctgctc ctcgtggggt cccacagatt gaagtcacct ttgagataga tgtgaatggt    1740
attcttcgag tgacagctga agacaagggt acagggaaca aaataagat cacaatcacc    1800
aatgaccaga atcgcctgac acctgaagaa atcgaaagga tggttaatga tgctgagaag    1860
tttgctgagg aagacaaaaa gctcaaggag cgcattgata ctagaaatga gttggaaagc    1920
tatgcctatt ctctaaagaa tcagattgga gataaagaaa agctgggagg taaactttcc    1980
tctgaagata aggagaccat ggaaaaagct gtagaagaaa agattgaatg gctggaaagc    2040
caccaagatg ctgacattga agacttcaaa gctaagaaga aggaactgga agaaattgtt    2100
caaccaatta tcagcaaact ctatggaagt gcaggccctc ccccaactgg tgaagaggat    2160
```

```
acagcagaaa aagatgagtt gtagacactg atctgctagt gctgtaatat tgtaaatact    2220
ggactcagga acttttgtta ggaaaaaatt gaaagaactt aagtctcgaa tgtaattgga    2280
atcttcacct cagagtggag ttgaactgct atagcctaag cggctgttta ctgcttttca    2340
ttagcagttg ctcacatgtc tttgggtggg gggggagaag aagaattggc catcttaaaa    2400
agcgggtaaa aaacctgggt tagggtgtgt gttcaccttc aaaatgttct atttaacaac    2460
tgggtcatgt gcatctggtg taggaagttt tttctaccat aagtgacacc aataaatgtt    2520
tgttatttac actggtcaaa aaaaaaaaaa aaaa                                2554
```